(12) United States Patent
Bar-Haim et al.

(10) Patent No.: US 10,709,867 B2
(45) Date of Patent: Jul. 14, 2020

(54) GAZE-CONTINGENT MUSIC REWARD THERAPY

(71) Applicant: RAMOT AT TEL-AVIV UNIVERSITY LTD., Tel Aviv (IL)

(72) Inventors: Yair Bar-Haim, Tel Aviv (IL); Amit Lazarov, Tel Aviv (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 281 days.

(21) Appl. No.: 15/808,192

(22) Filed: Nov. 9, 2017

(65) Prior Publication Data

US 2018/0126117 A1    May 10, 2018

Related U.S. Application Data

(60) Provisional application No. 62/420,183, filed on Nov. 10, 2016.

(51) Int. Cl.
*A61M 21/00* (2006.01)
*A61B 5/16* (2006.01)

(52) U.S. Cl.
CPC .............. *A61M 21/00* (2013.01); *A61B 5/16* (2013.01); *A61B 5/163* (2017.08); *A61M 2021/005* (2013.01); *A61M 2021/0027* (2013.01); *A61M 2205/3303* (2013.01); *A61M 2205/502* (2013.01); *A61M 2230/14* (2013.01)

(58) Field of Classification Search
CPC .......... A61M 21/00; A61M 2205/3303; A61M 2021/0027; A61M 2230/14; A61M 2021/005; A61M 2205/502; A61M 2230/005; A61B 5/16; A61B 5/163
See application file for complete search history.

(56) References Cited

U.S. PATENT DOCUMENTS

| | | | |
|---|---|---|---|
| 9,092,051 B2 * | 7/2015 | Park | G06F 3/01 |
| 2014/0206929 A1 * | 7/2014 | Anderson | A61M 21/00 600/28 |

OTHER PUBLICATIONS

Ferrari, Gina R. A. et al, "Can't Look Away: An Eye-Tracking Based Attentional Disengagement Training for Depression", Cognitive Therapy and Research, Oct. 2016, vol. 40, Issue 5, pp. 672-686.
Buckner, Julia D. et al, "Difficulty Disengaging Attention from Social Threat in Social Anxiety", Cognitive therapy and research, Feb. 1, 2010, vol. 34, No. 1, pp. 99-105.
(Continued)

*Primary Examiner* — Christine H Matthews
*Assistant Examiner* — Joshua Daryl D Lannu
(74) *Attorney, Agent, or Firm* — The Roy Gross Law Firm, LLC; Roy Gross (57) ABSTRACT

A computerized method for treating a psychopathological condition, the method comprising using at least one hardware processor for presenting to a patient on a computer display at least one visual media and at least audio media; receiving from an eye tracker a gaze direction of at least one eye of the patient; computing a display location of the gaze direction; and when a distance from the gaze location to a target location of the visual media is greater than a threshold value, pausing the audio media for a period of time.

18 Claims, 5 Drawing Sheets (56) References Cited

OTHER PUBLICATIONS

Armstrong, Thomas et al, "Eye tracking of attention in the affective disorders: A meta-analytic review and synthesis", Clinical Psychology Review, Dec. 2012, vol. 32, No. 8, pp. 704-723.

Lazarov, Amit et al, "Gaze-Contingent Music Reward Therapy for Social Anxiety Disorder: A Randomized Controlled Trial", The American Journal of Psychiatry, Jul. 2017; vol. 174, No. 7, pp. 649-656.

Bar-Haim, Yair, "Research Review: attention bias modification (ABM): a novel treatment for anxiety disorders", Journal of Child Psychology and Psychiatry, Aug. 2010, vol. 51, No. 8, pp. 859-870.

Schofield, Casey A. et al, "Social anxiety and difficulty disengaging threat: Evidence from eye-tracking", Cognition and Emotion, Feb. 2012, vol. 26, No. 2, pp. 300-311.

Lazarov, Amit et al, "Social anxiety is related to increased dwell time on socially threatening faces", Journal of Affective Disorders, Mar. 15, 2016, vol. 193, pp. 282-288.

Bar-Haim, Yair et al, "Threat-Related Attentional Bias in Anxious and Nonanxious Individuals: A Meta-Analytic Study", Psychological Bulletin, Jan. 2007, vol. 133, No. 1, pp. 1-24.

\* cited by examiner

GAZE-CONTINGENT MUSIC REWARD THERAPY

CROSS REFERENCE TO RELATED APPLICATIONS

This application claims priority to U.S. Provisional Patent Application No. 62/420,183, filed Nov. 10, 2016, entitled "Gaze-Contingent Music Reward Treatment for Social Anxiety Disorder: A Randomized Controlled Trial", which is incorporated herein by reference.

FIELD OF THE INVENTION

The invention relates to the field of cognitive neuroscience treatments.

BACKGROUND

Biased attentional processing of threat-related information may have a role in the etiology and maintenance of various psychopathologies including anxiety, mood disorders, post-traumatic stress disorder, eating disorders, autism spectrum disorders, substance-related and addictive disorders, and/or the like. Attention bias modification (ABM) may refer to treatment techniques in cognitive-neuroscience that target aberrant threat-related attention patterns in anxiety disorders and other psychopathologies as mentioned above.

Attention bias modification techniques may be based on reaction time (RT) paradigms that indicate that successful bias modification is associated with symptom reduction. However, efficacy of RT-based bias modification treatments may be inconsistent across techniques, possibly from a failure of some RT-based protocols to effectively engage aberrant attentional processes. RT measures of attention bias may possess poor psychometrics and may capture indirect effects of attention. This may be because RT-based indices of biases reflect behaviors occurring at the end of a complex process, which unfolds dynamically from the point of threat detection, thus failing to capture key aspects of attention allocation.

Moreover, RT-based ABM protocols may utilize many monotonous trials and may be experienced as tedious, potentially reducing treatment engagement. In contrast, eye-tracking measures may provide better therapeutic targets for attention bias modification. For example, relative to healthy controls, patients with social anxiety disorder (SAD) exhibit increased attentional dwelling on social threats and patients with major depressive disorder (MDD) dwell longer on dysphoric stimuli and less on positive stimuli, providing viable targets for therapeutic methods.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a computerized method for treating a psychopathological condition. The method comprises using at least one hardware processor for presenting, using an audio playback device, at least audio media to a patient. The method comprises using the hardware processor(s) for receiving, from an eye tracker, a gaze direction of at least one eye of the patient. The method comprises using the hardware processor(s) for computing a difference angle between a target direction and the gaze direction. The method comprises using the hardware processor(s) for, when the difference angle is greater than a threshold value, pausing the audio media for a period of time Optionally, the presenting further comprises presenting a visual media to a patient on a display.

Optionally, the visual media is at least one from a video, a digital video file, and at least one digital image.

Optionally, the visual media comprises images of faces.

Optionally, at least some of the images of faces depict neutral expressions, and at least some of the images of faces are threatening expressions, and the psychopathological condition is a social anxiety disorder.

Optionally, the psychopathological condition is at least one of a social anxiety disorder, an anxiety disorder, a mood disorder, a post-traumatic stress disorder, an eating disorders, a borderline personality disorder, an autism spectrum disorder, a substance-related disorder, psychotic disorder, and an addictive disorder.

Optionally, the audio media is at least one of a music track, a digital music file, a lecture track, a digital lecture file, an audio book, and a digital audio book.

Optionally, the period of time is between 0.1 second and 10 seconds.

Optionally, subsequent to the pausing, the audio media is rewound at least in part.

There is provided, in accordance with an embodiment, a computerized system for treating a psychopathological condition, the computerized system comprising an eye tracker, at least one hardware processor, a non-transitory computer-readable storage medium having program code embodied therewith. The program code is configured to be executable by said at least one hardware processor to present to the patient at least audio media. The program code is configured to receive, from the eye tracker, a gaze direction of at least one eye of the patient. The program code is configured to compute a difference angle between a target direction and the gaze direction. The program code is configured to, when the difference angle is greater than a threshold value, pause the audio media for a period of time.

Optionally, the computerized system further comprises a display for presenting images to a patient, and wherein the program code is further configured to present to a patient, on the display, at least one visual media.

Optionally, the visual media is at least one from a video, a digital video file, and at least one digital image.

Optionally, the visual media comprises images of faces.

Optionally, at least some of the images of faces are neutral expressions, and at least some of the images of faces arc threatening expressions, and the psychopathological condition is a social anxiety disorder.

Optionally, the psychopathological condition is at least one of a social anxiety disorder, an anxiety disorder, a mood disorder, a post-traumatic stress disorder, an eating disorders, a borderline personality disorder, an autism spectrum disorder, a substance-related disorder, and an addictive disorder.

Optionally, the audio media is at least one of a music track, a digital music file, a lecture track, a digital lecture file, an audio book, and a digital audio book.

Optionally, the period of time is between 0.1 second and 10 seconds.

Optionally, subsequent to the pausing the audio media is at least in part rewound.

There is provided, in accordance with an embodiment, a computer program product for treating a psychopathological condition, the computer program product comprising a non-transitory computer-readable storage medium having program code embodied therewith. The program code is configured to be executable by at least one hardware processor to present to the patient at least audio media. The program code is configured to receive, from an eye tracker, a gaze direction of at least one eye of the patient. The program code is configured to compute a difference angle between a target direction and the gaze direction. The program code is configured to when the difference angle is greater than a threshold value, pause the audio media for a period of time.

Optionally, the program code is further configured to present to a patient, on a display, at least one visual media.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Herein are disclosed computerized methods, systems, devices, and computer program products for treating psychopathologies associated with attention processing biases, such as anxiety, mood disorders, eating disorders, autism spectrum disorders, psychotic disorders, and substance-related disorders, and/or addictive disorders. By using music as a reward in an operant conditioning set-up, aberrant attentional gaze patterns may be rectified via gaze contingent music reward feedback. For example, a psychotherapy embodiment may involve: a) music as a reward; b) an operant conditioning procedure as a feedback method; c) continuous monitoring of the patient's eye-gaze at a visual media using eye-tracking technology.

The gaze-contingent music reward therapy (GC-MRT) may be applied using arrays of visual stimuli that match the typical stimuli associated with attentional bias for the treated disorder (e.g., multiple faces displays with different emotion expressions in anxiety and mood disorders; whole faces in autism spectrum disorder; images of alcoholic beverages in alcohol addiction; high caloric foods in anorexia nervosa).

Optionally, two visual areas of interest (AOIs) are defined—the non-target AOI (reflecting the area where patients of a certain disorder have been shown to typically over or under attend to relative to their healthy counterparts), and a target AOI. For example, social anxiety disorder is characterized by excessive attention to threat relative to neutral facial expressions: threat faces (disgust, anger) would constitute the non-target AOI whereas neutral faces would constitute the target AOI. For example, in patients with autism spectrum disorders, dwell time on the eyes area is typically shorter relative to other areas on the face, whereas healthy individuals pay more attention to the eyes. Thus, the area around the eyes would constitute the non-target AOI and the other areas of the face would be the target AOI. For example, the difference angle(s) between the gaze direction and the one or more target AOIs is computed. When the smallest difference angle is above a threshold, such as the gaze (as computed) is directed outside of the target AOI, a negative feedback is given, such as pausing of the music playback. Optionally, the gaze direction versus target AOI may be computed as an angle, a distance, a solid angle, an average angle, a series of angles, a distribution of angles, a distribution of distances, and/or the like. For example, alternative geometries and methods of measuring the directions criteria and threshold value/units may be used that are substantially equivalent.

Optionally, a computer display is used to display the visual media, such as a computerized slide show, a video file, a dynamically constructed HTML screen (i.e. using a browser window).

Optionally, the display is a hard copy display, a slide display, a photograph display, a book picture display, a Rorschach image display, and/or the like. For example, a hardcopy display is used for presenting the images, a sensor (such as a camera, a visual sensor, or a distance sensor, and/or the like) captures data depicting the location and orientation of the hardcopy display, and the AOIs are computed from the sensor data. For example, a hardcopy display is used to present visual data, and sensors connected to the computer (i.e. cameras), detect the geometric relationship between the hardcopy display and the eye tracking device for computing an angle between the target AOI and the gaze location on the display. For example, the hardcopy display is computer controlled. For example, the display is a televise connected to a video player, and the computer controls the video player.

Optionally, the music playback is by an analog playback device with digital controls that receive instructions (such as pause, play, rewind, and/or the like) from the hardware processor(s). For example, a computer controlled record player is used to perform the audio playback.

For each treatment session, patients may either select a music track they want to listen to during the session or a music track may be selected for them (this music serves as reward). The eye-tracking device may be calibrated to track the patent's gaze followed by a presentation of the disorder-relevant visual arrays. Patients may be instructed to freely look at the displays. Patients may hear the selected music play only when they are fixating on the target AOI (the area the protocol is designed to enhance attention to). When fixating on the non-target AOI, the music is not heard anymore, such as the music is paused, the playback volume is reduced, the music is stopped, and/or the like. Eye-tracking data are recorded throughout and based on the recorded fixation coordinates music feedback is provided.

Figure 1:
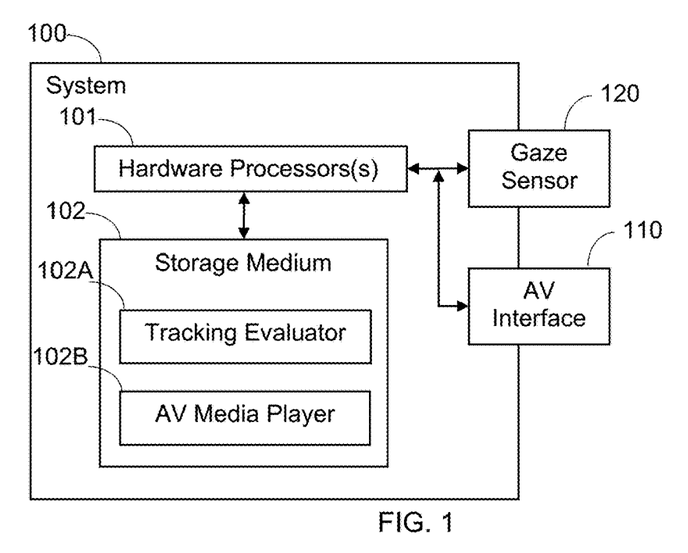
FIG. 1 shows schematically a system for gaze-contingent music reward.
Figure 2:
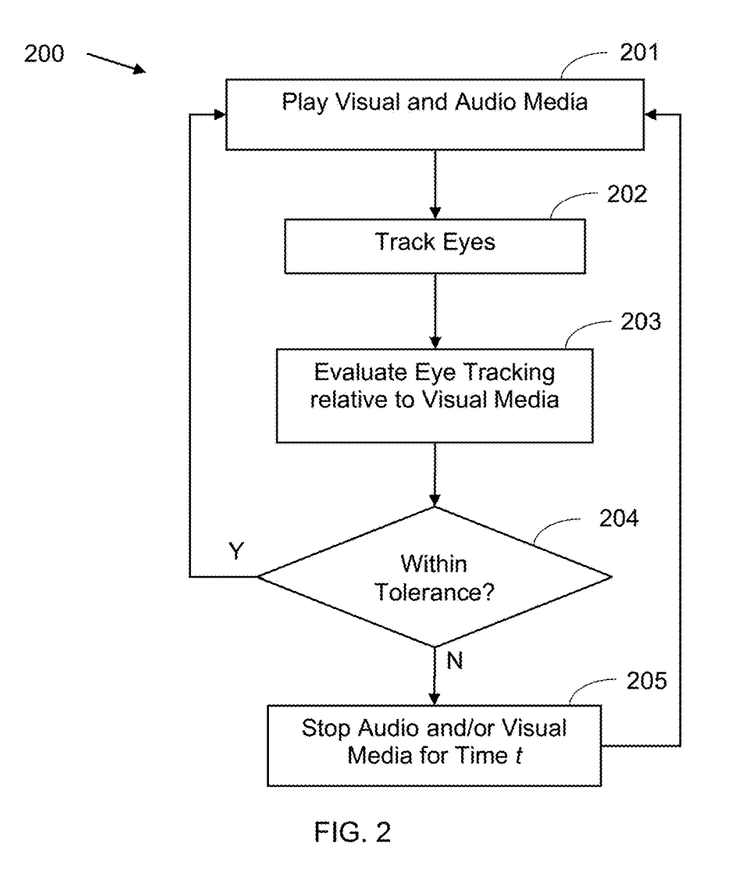
FIG. 2 shows a flowchart of a method for gaze-contingent music reward.

Reference is now made to FIG. 1 and FIG. 2, which show (i) schematically a system 100 and (ii) a flowchart 200 of a method, both for gaze-contingent music reward. System 100 comprises one or more hardware processors 101, a gaze sensor 120, an audio-visual (AV) interface 110, and a non-transitory, computer-readable storage medium 102. Storage medium 102 has encoded thereon program code, such as configured ion modules 102A and 102B, the program code configured to cause the hardware processor(s) 101 to perform at least some actions of an embodiment.

For example, an AV media player 102B plays 201 visual and audio media and a tracking evaluator 102A tracks 202 the gaze of the subject's one or more eyes. Tracking evaluator 102A may evaluate 203 the gaze direction relative to the visual media, such as visual media presented on a computer screen. When the gaze is within 204 a tolerance distance from the target gaze location (i.e. target AOI), the AV media player 102B may continue playing 201 the AV media. When the gaze location is not within 204 of a tolerance distance from the target gaze location, AV media player 102B may pause 205 the playback (such as stop, mute, reduce playback volume, and/or the like) of the audio and/or video media for a predefined time denoted t. For example, when a subject's gaze leaves the target gaze location on the screen, the music is paused for 5 seconds or until gaze is relocated to the targeted area.

Optionally, the screen is paused between 0.1 and 10 seconds. For example, a 0.1 second pause may cause a jitter in the audio file, a frequency change, and/or the like. For example, the larger the distance the patient's gaze is from the target AOI (target gaze location), such as the area of interest, the larger the pause.

Optionally, after a pause is performed, the audio media is rewound. For example, after a pause an audio music track is rewound a few seconds, so the music is less interrupted. For example, after a pause a digital audio book is rewound to the beginning of a chapter, a beginning of a sentence, a beginning of the book, or the like, so that the patient is further motivated to perform the gaze direction treatment as requested and avoid interruption to the audio media playback. Optionally, the rewind is between 0.1 seconds and 100 seconds.

The visual media may be an analog media, such as a slide or a picture book, a digital media, such as a digital image, a collage of digital images, an array of digital images, and/or the like. For example, the eye tracker is combined with a camera, and a patient looks at a picture book while the eye tracker compares the gaze location with the book location, so that the computer can evaluate which image in the picture book is being looked at by the patient.

The audio media may be an analog audio tape, record, or the like, that is played by a digital player that can accept commands to play, pause, rewind, and/or the like from the computer. The audio media may be a digital media, such as a digital music, file, a digital audio book file, a lecture on a digital MP3 file, and/or the like, and the playback of the media is through headphones and/or loudspeakers connected to an audio card of the computer.

The audio media may be used in the above example embodiment as a positive feedback, where the feedback is controlled by the gaze direction. Optionally, the positive feedback may be a non-audio positive feedback. For example, a haptic feedback may be incorporated such that a massage is given to the feet of a deaf patient, and when the patient's gaze strays from the allowed regions of the display, the massage is stopped.

Optionally, a negative feedback may be controlled by the gaze direction. For example, when the patient's gaze strays from the allowed regions of the display, an electrical stimulus is given to shock a limb of the patient, causing a slight discomfort. For example, when the patient's gaze strays from the allowed regions of the display, an audible alarm is sounded to the patient, causing a slight discomfort. Optionally, a combination of positive and negative feedbacks may be used. For example, when the patient gazes at the allowed region music is played, but when the patient's gaze strays from the allowed regions of the display, an audible alarm is sounded to the patient, causing a slight discomfort. Optionally, positive and/or negative feedbacks are provided through at least one patient sense, such as auditory, visual, olfactory, touch, proprioception, and/or the like. Optionally, positive and/or negative feedbacks are provided through penalty and/or reward incentives, such as physical, emotional, social, monetary, and/or the like rewards. For example, a participant may gain or lose points/money.

Experimental Results

A randomized control trial (RCT) was performed, to test the efficacy and associated mechanism of an eye-tracking-based ABM treatment for social anxiety disorder (SAD), targeting enhanced dwell-time on threat faces in SAD. Patients were randomized to either gaze-contingent music reward therapy (GC-MRT), designed to divert attention toward neutral over threatening faces, or a placebo control (PC) condition with no feedback on viewing patterns. The RCT tested the hypotheses that compared to PC, GC-MRT may result in: a) more robust, lasting reductions in SAD symptoms monitored over a four-month period; b) greater reduction in dwell-time on threat; and c) the reduction in dwell-time on threat may partially mediate the association between treatment group and reductions as measured by SAD symptoms. Clinician and self-report measures of social anxiety were acquired pre-treatment, post-treatment, and at 3-month follow-up. Dwell-time on socially-threatening faces was assessed during the training sessions and at pre- and post-treatment.

Results show that GC-MRT yielded greater SAD symptom reductions than PC on both clinician-rated and self-reported measures. Therapeutic effects were maintained at follow-up evaluations. GC-MRT, but not PC, reduced dwell-time on threats, which partially mediated clinical effects. GC-MRT also altered dwell-time on threat faces not used in training, reflecting near-transfer training generalization.

Participants in the RCT were 40 treatment-seeking patients (Mage=33.83, SD=0.10.80; 20 males). Inclusion criteria were: a) primary diagnosis of SAD (i.e., SAD being the main source of behavioral and emotional dysfunction); b) 18-60 years of age; and c) normal or corrected-to-normal vision. Exclusion criteria were: a) any history or present diagnosis of psychosis; h) high risk for violence to self or others; c) present diagnosis of post-traumatic stress disorder, obsessive-compulsive disorder, bipolar disorder, or tic disorder; d) epilepsy or brain injury; e) use of medication other than SSRIs; f) any concurrent psychotherapy; g) drug or alcohol misuse; and h) eye-tracking calibration difficulties.

The participants were characterized by co-morbidities: 11 participants had mild depressive episode (7 participants in the GC-MRT group), 9 participants had dysthymia (4 participants in the GC-MRT group), 16 participants generalized anxiety disorder (7 participants in GC-MRT), 6 participants panic disorder (2 participants in GC-MRT), and 4 participants agoraphobia (2 participants in GC-MRT). Nine participants (5 participants in GC-MRT) were using a stable dose of SSRIs, starting at least three months prior to the beginning of the study. SSRI dose was kept stable throughout the study. Participants were randomly assigned to either GC-MRT (n=20) or PC (n=20). The two groups did not differ in age, education, and symptoms severity at baseline, and had the same male/female ratio (50% male). All participants were naïve to eye-tracking procedures. All participants continued participation until the end of treatment, and three from the PC group declined participation in the follow-up. The study was approved by the local Institutional Review Board and participants provided written informed consent.

Potential participants who sought treatment through the study were screened over the phone for social anxiety symptoms using the Social Phobia Inventory (SPIN). For example, 337 subjects were screened, and 257 did not meet inclusion criteria. Those with SPIN scores ≥30 (probable SAD) were invited for a full clinical assessment. Clinical interviews were conducted by an independent evaluator, a clinical psychologist trained to 85% reliability with a senior psychologist. The independent evaluator was blind to group assignment and all aspects of treatment. Weekly sessions were conducted to monitor and review diagnostic decisions.

Primary and co-morbid diagnoses were ascertained using the Mini-International Neuropsychiatric Interview (MINI), and further established using the clinician-rated Liebowitz Social Anxiety Scale (LSAS), with a cutoff score ≥50 as inclusion criterion. This cutoff represents an optimal balance between specificity and sensitivity for SAD diagnosis. For example, 80 subjects were assessed, and 40 were excluded, such as 26 did not meet inclusion criteria, 11 declined to participate, and 3 failed eye tracking calibration.

Primary outcome was severity of social anxiety measured using the total score of the clinician-administered LSAS. Cronbach's α in our sample was 0.86, 0.87, and 0.86 at pre-treatment, post-treatment, and follow-up, respectively. Secondary outcome was self-reported social anxiety using the SPIN total score. Cronbach's a in this sample was 0.86, 0.90, and 0.89 at pre-treatment, post-treatment, and follow-up, respectively.

Attention allocation to threat was assessed with an established eye-tracking task, using a remote high-speed eye-tracker (SensoMotoric Instruments, Inc., Teltow, Germany). Each trial presented a 4×4 matrix of 16 faces, half with disgusted and half with neutral facial expressions.

Figure 3:
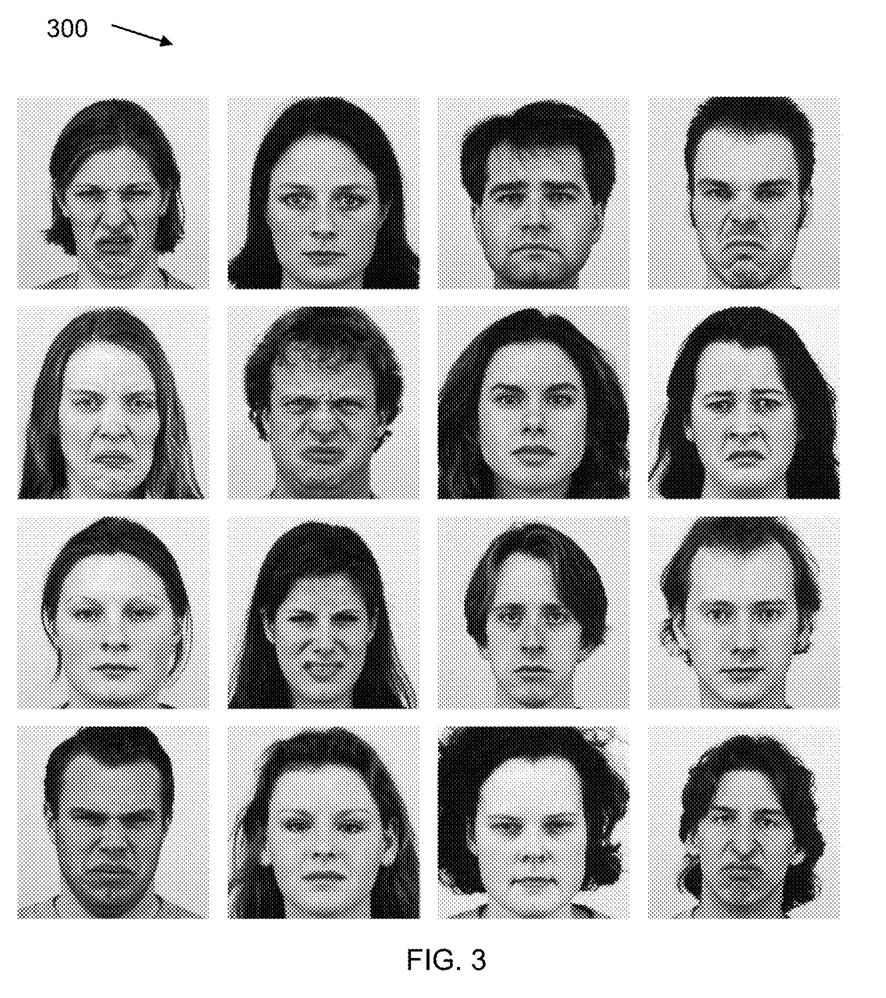
FIG. 3 shows a partial display of a user interface for gaze-contingent music reward.

Reference is now made to FIG. 3, which shows a partial display 300 of a user interface for gaze-contingent music reward. Each face appeared randomly at any position on the matrix while ensuring the following: a) each actor appeared only once in a matrix; b) each matrix contained eight male and eight female faces; c) half the faces were disgusted and half neutral; and d) the four inner faces were always two disgusted and two neutral.

Each trial began with a fixation-cross shown until a fixation of 1000 milliseconds (ms) was recorded, verifying that a trial began only when participants' gaze was fixated at the matrix's center. Each matrix was presented for 6000 ms, followed by an inter-trial interval of 2000 ms until the next fixation cross appeared. Participants were instructed to look freely at each matrix in any way they chose until it disappeared. For full detail see online supplementary. Cronbach's a for proportion of dwell time on threat in this sample was 0.94 at pre-treatment (full sample), and 0.95 and 0.93 at post-treatment for the GC-MRT and PC group, respectively.

The treatment task was a modified version of the assessment task described above designed to divert patients' attention toward the neutral and away from the threat faces presented in the matrices. At the beginning of each treatment, patients selected a 12-minute music track they wanted to listen to during the session. Music tracks were selected from an extensive menu reflecting the most popular musicians according to published rating charts. Each treatment session began with eye-tracking calibration and validation followed by 30 face matrices, 24 seconds each, with no inter-trial intervals. Each face appeared 15 times per session. Patients in the GC-MRT group heard their selected music play only when fixating on one of the neutral faces in a matrix (neutral area of interest, AOI). When fixating on one of the disgusted faces (the threat AOI) the music stopped. Patients in the PC group heard the music of their choice throughout the session without interruptions (i.e., non-contingent upon their eye-gaze). The treatment tasks ran E-Prime version 2 (Psychology Software Tools, Pittsburgh, USA).

Gaze location data were recorded using a RED500 system and analyzed with BeGaze software (SensoMotoric Instruments, Inc., Teltow, Germany). Operating distance to the eye-tracking monitor was 70 cm. The stimuli were presented on a 22-inch Dell P2213 monitor (screen resolution 1680× 1050). Sampling rate was 500 Hz. For each matrix two AOIs were defined: the 8 disgust faces (threat AOI), and the 8 neutral faces (neutral AOI). Total dwell-time in milliseconds for each AOI in each matrix was recorded, and the proportion of dwell-time on the threat AOI relative to total dwell-time on both AOIs in each matrix was calculated, reflecting the proportion of time gaze was on threat stimuli out of the total time the faces on each matrix were observed. An overall index of average percent dwell-time on threat was computed across the presented matrices (60 and 30 in the assessment and training tasks, respectively).

Study design was a parallel-group RCT, with two groups (GC-MRT, PC) and three assessment points (pre-treatment, post-treatment, 3-month follow-up). Participants were clinically assessed at the three timepoints using structured clinician-rated measures and self-report questionnaires. Attention allocation patterns were assessed at pre- and post-treatment and across the training sessions.

Consenting participants underwent the clinical assessment at pre-treatment. They were informed that the purpose of the study was to evaluate the efficacy of a novel eye-tracking-based treatment for SAD. Those meeting the inclusion criteria completed the attention allocation assessment task in a subsequent session the following week. Treatment consisted of eight 20-minute sessions, twice a week over four weeks. Post-treatment assessment was conducted one week after the last training session and included the same measures and tasks used in the pre-treatment assessment. Participants were clinically re-assessed again at a 3-month follow-up. At this point participants in the PC group were given the opportunity to receive GC-MRT.

Independent samples t-tests were used to compare between-groups descriptive characteristics at pre-treatment. Treatment effects were tested using Generalized Estimating Equations (GEE), as recommended for RCTs. GEE accounts for correlated repeated-measurements and accommodates missing data under the missing-at-random assumption, by computing estimated marginal means and thus serves as an intention-to-treat analysis strategy which includes data from all randomized participants who provided at least one data point. To represent within-subject dependencies in the models, we specified an unstructured correlation matrix. Overall effects of GC-MRT relative to PC on clinician-rated (LSAS total score as well as the fear and the avoidance sub-scale scores) and self-reported (SPIN) social anxiety symptoms were estimated using models containing main effects of group (GC-MRT, PC), time (pre-treatment, post-treatment, follow-up), and their interaction. We first applied a full factorial model across the three timepoints. Follow-up analyses modeled symptom change from pre- to post-treatment. Long-term maintenance effects modeled symptom change from post-treatment to follow-up. Time-by-group interaction terms tested the treatment effect hypothesis of greater decrease in SAD symptoms over time for the GC-MRT group relative to the PC group. Chi-square tests were used to compare groups on clinically significant change (CSC).

Effects of training group on attention allocation were analyzed using repeated-measures analysis of variance (ANOVA) on percent dwell-time on threat during the treatment task in Sessions 1 through 8. Session, served as a within-subject factor and treatment group (GC-MRT, PC) as a between-subjects variable. An independent samples t-test was also used to compare the two groups on the amount of reduction in percent dwell-time on threat from Session 1 to Session 8, calculated as percent dwell-time on threat in Session 1 minus percent dwell-time on threat in Session 8. To test for possible group differences in percent dwell-time on threat at pre-treatment we compared group performance using independent samples t-tests on: a) the pre-treatment assessment task; and b) the first five matrices of Session 1.

To examine generalization of training through near transfer to novel faces, repeated-measures ANOVA modeled percent dwell-time on threat in the assessment task. Time (pre-treatment, post-treatment) served as a within-subject factor and treatment group (GC-MRT, PC) served as a between-subjects variable. Follow-up analyses included separate contrasts for the pre- and post-treatment assessments. All statistical tests were 2-sided, using $\alpha \leq 0.05$. Effect sizes are reported using $\eta 2p$ and Cohen's d when appropriate.

Finally, to assess whether reduction in dwell-time on threat (Session 8 minus Session 1) served as a mediator of treatment effects as measured by the LSAS and SPIN, we applied a mediation analysis procedure, model 4, using the PROCESS macro in SPSS (SPSS Inc., Chicago, Ill.). This procedure estimates indirect effects in both un-moderated and moderated mediation models, providing bootstrap confidence intervals (CIs) for the mediated effects. We applied 1,000 bootstrap samples. The mediator variables are considered significant when the lower and upper bounds of the CI do not include zero.

TABLE 1

Demographic Characteristics, Social Anxiety Symptoms, and Attention Allocation Patterns by Group at Pre-treatment, Post-treatment, and Follow-Up

| Demographics | GC-MRT group | | PC group | |
|---|---|---|---|---|
| | M | SD | M | SD |
| Age | 33.90 | 9.91 | 33.77 | 11.89 |
| Years of education | 14.42 | 3.42 | 13.8 | 2.54 |
| LSAS (pre-treatment) | 78.05 | 13.74 | 74.15 | 20.11 |
| LSAS (post-treatment) | 49.60 | 16.78 | 66.70 | 26.45 |
| LSAS (follow-up) | 50.25 | 15.64 | 58.84 | 27.35 |
| SPIN (pre-treatment) | 47.75 | 7.28 | 44.3 | 10.04 |
| SPIN (Post-treatment) | 31.7 | 7.17 | 40.5 | 12.22 |
| SPIN (follow-up) | 27.00 | 8.22 | 33.90 | 14.32 |
| Dwell time (pre-treatment) | 48.54 | 7.75 | 46.86 | 9.34 |
| Dwell time (post-treatment) | 37.90 | 11.53 | 46.32 | 4.83 |

The two groups did not differ in age, education, self- and clinician-reported SAD symptoms, and percent dwell-time on threat faces at pre-treatment, all p-values >0.22 (TABLE 1).

Figure 4A:
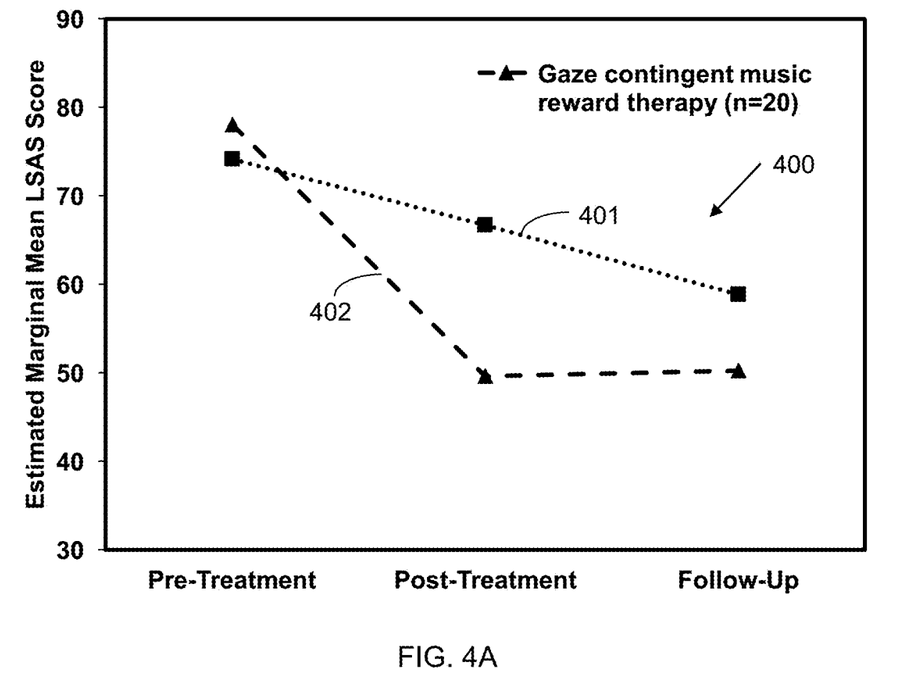
FIG. 4A shows a first graph of experimental results for a gaze-contingent music reward embodiment.

Change in Social Anxiety Symptoms Following Treatment: Primary Outcome (LSAS). Reference is now made to FIG. 4A, which shows a first graph 400 of experimental results for a gaze-contingent music reward embodiment. FIG. 4A illustrates results of the GEE model for LSAS scores. A main effect of time, Wald=75.92, p-value <0.0001, was subsumed under a significant time-by-group interaction effect, Wald=18.13, p-value <0.0001. Follow-up analyses indicated significant reduction from pre- to post-treatment in both groups 401 and 402, p-value <0.0001, d=1.86 for GC-MRT, and p-value <0.05, d=1.06 for PC. However, reduction in SAD severity was significantly larger in the GC-MRT group relative to the PC group, Wald=18.04, p-value <0.0001. This difference reflected a mean change in LSAS score that is 21 points larger for GC-MRT relative to PC, d=1.31. Modeling change in symptoms from post-treatment to 3-month follow-up reveled no change in symptoms in the GC-MRT group, p-value=0.75. In the PC group symptoms continued to decrease, p-value=0.021, Wald=4.77, p-value <0.03, d=1.09. This difference reflected a mean change in LSAS score that is 8.51 points larger for PC relative to GC-MRT. A similar result pattern was observed for the fear and the avoidance LSAS subscales when analyzed separately (see online Supplement).

The number of participants who achieved clinically significant change (CSC) from pre- to post-treatment was compared between the two treatment groups 401 and 402. Determination of CSC reflected known the test-retest reliability data and pre-treatment LSAS scores from the authors' data pool in previous clinical trials (N=87 subjects). A post-treatment cutoff score of 44.09 was determined as reflecting CSC. 14 patients (70%) in the GC-MRT group 402 vs. 6 patients (30%) in the PC group 401 achieved CSC post-treatment, $\chi 2=6.40$, p-value=0.01. Analysis of CSC at follow-up showed that 15 patients (75%) in the GC-MRT group vs. 6 patients (30%) in the PC group achieved CSC, $\chi 2=8.12$, p-value=0.004.

Figure 4B:
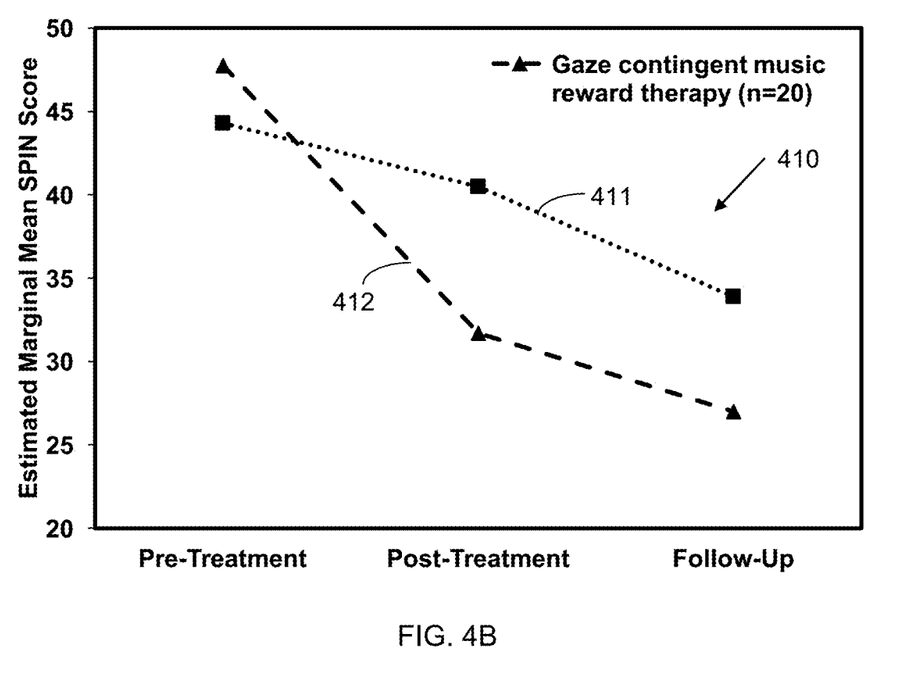
FIG. 4B shows a second graph of experimental results for a gaze-contingent music reward embodiment.

Reference is now made to FIG. 4B, which shows a second graph 410 of experimental results for a gaze-contingent music reward embodiment. FIG. 4B depicts results from the GEE model for self-reported SPIN scores. This revealed a main effect of time, Wald=81.82, p-value <0.0001, subsumed under a group-by-time interaction, Wald=16.13, p-value <0.0001. Follow-up analyses indicated a significant reduction from pre- to post-treatment in the GC-MRT group 412, p-value <0.0001, d=1.76, but not in the PC group 411, p-value=0.12. Reduction in SAD severity from pre- to post-treatment was significantly larger in GC-MRT relative to PC, Wald=16.12, p-value <0.0001. This difference reflected a mean change in SPIN score that is 12.29 points larger for GC-MRT relative to PC, d=1.24. For change in symptoms from post-treatment to follow-up, only a main effect of time emerged, Wald=23.17, p-value <0.0001, with both groups showing further improvement, p-values <0.0001 and 0.001, ds=1.23 and 1.09, for the GC-MRT and PC groups, respectively. The time-by-group interaction was non-significant, Wald=0.81, p-value=0.37.

Figure 5A:
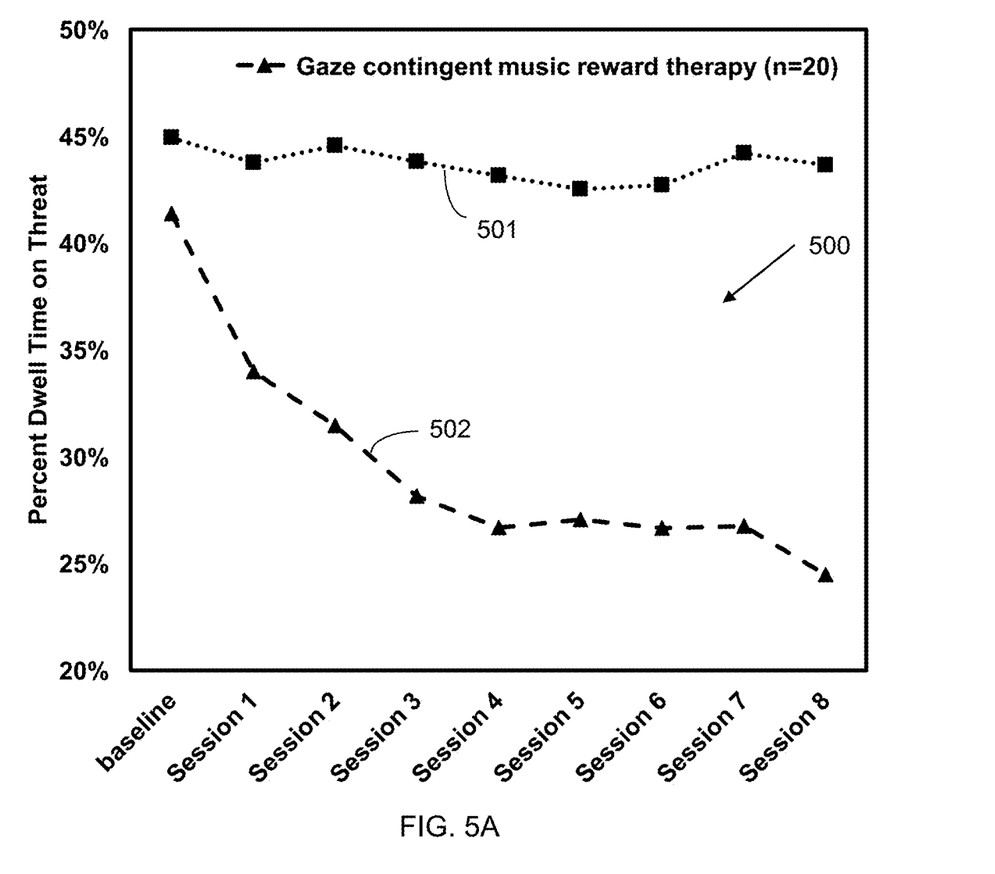
FIG. 5A shows a third graph of experimental results for a gaze-contingent music reward embodiment.

Reference is now made to FIG. 5A, which shows a third graph 500 of experimental results for a gaze-contingent music reward embodiment. Percent dwell-time on threat by group and session is depicted in graph 501. A comparable performance in the GC-MRT (M=41.38, SD=11.77) and PC (M=44.92, SD=8.19) groups was observed for average dwell-time on threat in the first five matrices of Session 1, $t(38)=1.10$, p-value=0.27. Analyses across sessions revealed significant main effects of group, $F(1, 38)=20.16$, p-value <0.001, $\eta 2p=0.35$, and session, $F(7, 266)=3.42$, p-value <0.001, $\eta 2p=0.08$, subsumed under a significant group-by-session interaction, $F(7, 266)=2.36$, p-value=0.02, $\eta 2p=0.05$. Percent dwell-time on threat reduced by 9% from Session 1 to Session 8 in the GC-MRT group 502 relative to 0.1% in the PC group 501, $t(38)=2.70$, p-value=0.01, $d=0.86$.

Figure 5B:
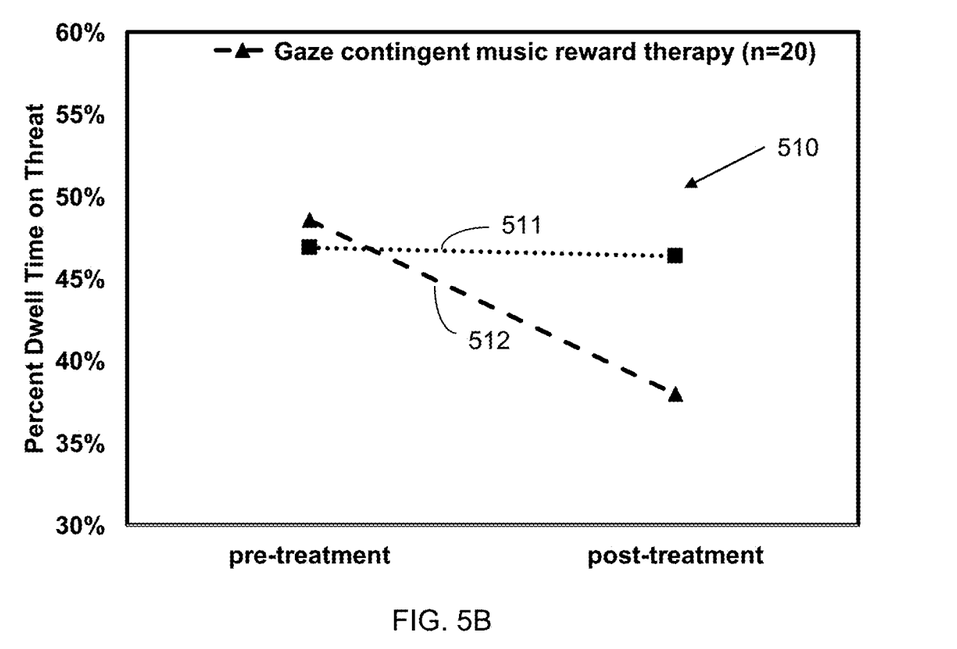
FIG. 5B shows a fourth graph of experimental results for a gaze-contingent music reward embodiment.

Reference is now made to FIG. 5B, which shows a fourth graph 510 of experimental results for a gaze-contingent music reward embodiment. Percent dwell-time on threat by group (GC-MRT 512, PC 511) and time (pre-, post-treatment) is depicted in graph 511. A main effect of time, $F(1, 34)=7.52$, p-value <0.01, $\eta 2p=0.18$, was qualified by a significant group-by-time interaction, $F(1, 34)=4.63$, p-value=0.04, $\eta 2p=0.12$. Follow-up contrasts revealed no group differences at pre-treatment, $F(1, 34)=0.05$, p-value=0.82, $\eta 2p$-value <0.01. At post-treatment, significantly less dwelling on threat was noted in the GC-MRT group 512 relative to the PC group 511, $F(1, 34)=7.84$, p-value <0.01, $\eta 2p=0.19$, with the PC group ($M=46.32$, $SD=4.83$) allocating more attention to threat compared with the GC-MRT group ($M=37.90$, $SD=11.53$).

Reduction in dwell-time on threat from Session 1 to Session 8 partially mediated the association between group and reduction in clinician-reported LSAS scores from pre- to post-treatment. The effect of group on reduction in dwell-time on threat was significant ($B=9.37$, $SE=3.49$, p-value <0.05, $CI95=0.02, 0.16$). The effect of reduction in threat dwell-time on LSAS reduction was not significant ($B=34.02$, $SE=23.25$, p-value=0.15), but the indirect effect of group on the reduction in LSAS scores via the reduction in dwell-time on threat was significant ($ab=3.16$, $SE=1.87$, p-value <0.05, $CI95=0.27, 7.98$), reflecting a partial mediation effect. A similar analysis on self-reported SPIN scores from pre- to post-treatment did not reveal mediation via reduction in threat dwell-time. The effect of reduction in threat dwell-time on SPIN reduction was not significant ($B=10.31$, $SE=14.64$, p-value=0.15), and although the direct effect of group on reduction in SPIN scores was significant ($B=11.29$, $SE=3.43$, p-value <0.05, $CI95=4.34, 18.25$), the indirect effect via a reduction in dwell-time on threat was not ($ab=0.96$, $SE=1.47$, $p>0.05$).

This RCT examined the efficacy of a novel gaze-contingent music reward treatment (GC-MRT) for patients with SAD. To our knowledge, it is the first study to apply gaze-contingent reward feedback treatment in a clinically anxious population. Results indicate that GC-MRT was significantly more effective than a PC condition in reducing both clinician-rated and self-reported SAD symptoms post-treatment. Moreover, overall symptom reduction reflected reductions in experienced social fear and avoidance behaviors, as reflected in LSAS subscales. GC-MRT effects were maintained at 3-month follow-up, though patients in the PC condition did tend to improve during this period. Findings also indicate effective target engagement in the GC-MRT group, a near-transfer of this target engagement effect, and partial mediation of clinical effects by effects on target engagement. However, this partial mediation was not significant for self-reported social anxiety.

While GC-MRT is based on the principles of attention bias modification (ABM), this novel treatment involves several unique features. First, training targets a behavior, dwell-time on threat in a free-viewing paradigm, with acceptable psychometrics, which has been missing from most RT-based ABMs. Second, unlike most forms of ABM, the stimulus array in GC-MRT contains 16 faces per matrix, thereby increasing the requirement for continuous allocation of attention away from negative stimuli. This also increases ecological validity relative to ABM tasks containing smaller stimulus arrays. Third, GC-MRT targets eye-gaze, which reflects dynamic allocation of attention to stimuli, unlike most forms of ABM, which target RT-based biases, a less dynamic measure occurring at the end of complex information processing progressions. Finally, the use of music in GC-MRT and PC may increase patients' engagement. Of note, the current study maintained 100% of patients in the trial, which is unusual. This may address concerns expressed about poor engagement in other forms of ABM.

Although results indicated a lower LSAS score in GC-MRT relative to PC at post-treatment, there was also a significant reduction in symptoms amongst the PC group at post-treatment and follow-up. This might reflect nonspecific placebo effects as the two conditions were equivalent with regard to number of sessions, session length, intervention modality, and the amount and nature of interaction with research stuff. Prior research has documented positive clinical effects of well-designed placebo conditions in clinical trials. Alternatively, symptom reduction in the PC group may be related to exposure to threat faces in the context of positive valence induced by the music reward. Previous fear-conditioning, extinction, and exposure therapy research in anxiety has raised the possibility that reducing the negative valance of a feared stimulus, and increasing positive affect prior to and during exposure, may increase the beneficial outcome of exposure in anxiety.

These results may indicate promising efficacy of GC-MRT, some general limitations of this method deserve notice. First, use of eye-tracking restricts treatment for those who do not have eye-tracking calibration difficulties. In the current sample three patients failed to calibrate and others were not invited due to eye-sight issues that would have prevented successful calibration. Second, although eye-tracking technology is advancing rapidly, high quality eye-tracking setups are still quite costly and thus might restrict availability in clinics.

The current RCT study examined a newly developed ABM based on gaze-contingent feedback targeting a previously identified bias in SAD-increased dwell-time on socially threatening stimuli. GC-MRT, comprised of eight 12-min sessions of gaze-contingent music reward feedback, was able to successfully rectify this biased gaze process. Moreover, this achieved reduction in dwell-time on threat led to a significant reduction in SAD symptoms following treatment. Additional research is needed to confirm these findings and to possibly extend them to other anxiety and affective disorders.

The above experimental results, as well as any portion thereof, constitute optional embodiments of the present invention.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computerized method for treating a psychopathological condition, the method comprising using at least one hardware processor for:
   presenting, using an audio playback device, at least audio media to a patient;
   receiving, from an eye tracker, a gaze direction of at least one eye of the patient;
   computing a difference angle between a target direction and the gaze direction; and
   pausing the audio media for a period of time, based, at least in part, on said computing,
   wherein subsequent to the pausing, the audio media is at least in part rewound.

2. The computerized method of claim 1, wherein the presenting further comprises presenting a visual media to the patient on a display.

3. The computerized method of claim 2, wherein the visual media is at least one from a video, a digital video file, and at least one digital image.

4. The computerized method of claim 2, wherein the visual media comprises images of faces.

5. The computerized method of claim 4, wherein at least some of the images of faces depict neutral expressions, and at least some of the images of faces are threatening expressions, and the psychopathological condition is a social anxiety disorder.

6. The computerized method of claim 1, wherein the psychopathological condition is at least one of a social anxiety disorder, an anxiety disorder, a mood disorder, a post-traumatic stress disorder, an eating disorders, a borderline personality disorder, an autism spectrum disorder, a substance-related disorder, psychotic disorder, and an addictive disorder.

7. The computerized method of claim 1, wherein the audio media is at least one of a music track, a digital music file, a lecture track, a digital lecture file, an audio book, and a digital audio book.

8. The computerized method of claim 1, wherein the period of time is between 0.1 second and 10 seconds.

9. A computerized system for treating a psychopathological condition, the computerized system comprising:
   an eye tracker;
   at least one hardware processor; and
   a non-transitory computer-readable storage medium having program code embodied therewith, the program code executable by said at least one hardware processor to:
   (i) present to a patient at least audio media;
   (ii) receive, from the eye tracker, a gaze direction of at least one eye of the patient;
   (iii) compute a difference angle between a target direction and the gaze direction; and
   (iv) pause the audio media for a period of time based, at least in part, on said computing,
   wherein subsequent to the pausing, the audio media is at least in part rewound.

10. The computerized system of claim 9, further comprising a display for presenting images to said patient, and wherein the program code is further configured to present to said patient, on the display, at least one visual media.

11. The computerized system of claim 10, wherein the visual media is at least one from a video, a digital video file, and at least one digital image.

12. The computerized system of claim 10, wherein the visual media comprises images of faces.

13. The computerized system of claim 12, wherein at least some of the images of faces are neutral expressions, and at least some of the images of faces are threatening expressions, and the psychopathological condition is a social anxiety disorder.

14. The computerized system of claim 9, wherein the psychopathological condition is at least one of a social anxiety disorder, an anxiety disorder, a mood disorder, a post-traumatic stress disorder, an eating disorder, a borderline personality disorder, an autism spectrum disorder, a substance-related disorder, and an addictive disorder.

15. The computerized system of claim 9, wherein the audio media is at least one of a music track, a digital music file, a lecture track, a digital lecture file, an audio book, and a digital audio book.

16. The computerized system of claim 9, wherein the period of time is between 0.1 second and 10 seconds.

17. A computer program product for treating a psychopathological condition, the computer program product comprising a non-transitory computer-readable storage medium having program code embodied therewith, the program code executable by at least one hardware processor to:
   present to a patient at least audio media;
   receive, from an eye tracker, a gaze direction of at least one eye of the patient;
   compute a difference angle between a target direction and the gaze direction; and
   pause the audio media for a period of time based, at least in part, on said computing,
   wherein subsequent to the pausing, the audio media is at least in part rewound.

18. The computer program product of claim 17, wherein the program code is further configured to present to said patient, on a display, at least one visual media.

* * * * *